(12) United States Patent
Shigaki et al.

(10) Patent No.: US 10,101,259 B2
(45) Date of Patent: Oct. 16, 2018

(54) FLOW ANALYZER, FLOW CYTOMETER AND FLOW ANALYZING METHOD

(71) Applicant: NIHON KOHDEN CORPORATION, Tokyo (JP)

(72) Inventors: Naoki Shigaki, Tokyo (JP); Shinji Yamamori, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 323 days.

(21) Appl. No.: 14/919,872

(22) Filed: Oct. 22, 2015

(65) Prior Publication Data

US 2016/0125615 A1    May 5, 2016

(30) Foreign Application Priority Data

Oct. 31, 2014    (JP) .................. 2014-222144

(51) Int. Cl.
*H04N 5/225* (2006.01)
*G01N 15/14* (2006.01)
*G06K 9/46* (2006.01)
*G06K 9/52* (2006.01)
(Continued)

(52) U.S. Cl.
CPC ......... *G01N 15/14* (2013.01); *G01N 15/1404* (2013.01); *G06K 9/4604* (2013.01); *G06K 9/4642* (2013.01); *G06K 9/52* (2013.01); *G06T 7/62* (2017.01); *G01N 2015/1006* (2013.01); *G01N 2015/1409* (2013.01);
(Continued)

(58) Field of Classification Search
CPC ...... G06K 9/4604; G06K 9/52; G06K 9/4642; G01N 15/15; G01N 2015/1415; G01N 2015/1006; G01N 2015/1409; G01N 2015/1413; G01N 15/1404; G06T 2207/30024; G06T 7/62
USPC ............................................. 348/79
See application file for complete search history.

(56) References Cited

U.S. PATENT DOCUMENTS

| 4,393,466 A | 7/1983 | Deindoerfer et al. |
| 4,612,614 A | 9/1986 | Deindoerfer et al. |
| 4,732,479 A | 3/1988 | Tanaka et al. |

(Continued)

FOREIGN PATENT DOCUMENTS

| JP | S60-038653 A | 2/1985 |
| JP | S62-100643 A | 5/1987 |

(Continued)

OTHER PUBLICATIONS

Japanese Office Action issued in Patent Application No. JP-2014-222144 dated Dec. 5, 2017.

*Primary Examiner* — Nguyen Truong
(74) *Attorney, Agent, or Firm* — Pearne & Gordon LLP

(57) ABSTRACT

A flow analyzer includes a flash lamp configured to irradiate a flow cell having a flow path with flash light, the flow path having a predetermined width, an imaging section configured to take images of the flow cell that is irradiated by the flash lamp such that the predetermined width is included in an imaging range, an evaluator configured to detect edges indicating respective sides of the flow cell from an image of a fluid that is taken by the imaging section and to evaluate the fluid passing through the flow cell based on a relationship between a width between the detected edges and the predetermined width, and an output section configured to output a result of the evaluation by the evaluator.

14 Claims, 9 Drawing Sheets

(51) Int. Cl.
*G06T 7/62* (2017.01)
*G01N 15/10* (2006.01)

(52) U.S. Cl.
CPC ............... *G01N 2015/1413* (2013.01); *G01N 2015/1415* (2013.01); *G06T 2207/30024* (2013.01)

(56) References Cited

U.S. PATENT DOCUMENTS

| | | | |
|---|---|---|---|
| 5,159,403 A | 10/1992 | Kosaka | |
| 2009/0153883 A1 | 6/2009 | Shinoda | |
| 2009/0219530 A1 | 9/2009 | Mitchell et al. | |
| 2009/0244536 A1 | 10/2009 | Mitchell et al. | |
| 2010/0020321 A1 | 1/2010 | Furuki et al. | |
| 2011/0155927 A1 | 6/2011 | Mitchell et al. | |
| 2011/0222051 A1 | 9/2011 | Heng | |
| 2012/0012757 A1 | 1/2012 | Mitchell et al. | |
| 2012/0076349 A1 | 3/2012 | Manri et al. | |
| 2012/0140223 A1 | 6/2012 | Mitchell et al. | |
| 2013/0314526 A1* | 11/2013 | Yasuda | G01N 15/1475 348/79 |
| 2014/0220621 A1* | 8/2014 | Durack | G01N 15/1427 435/34 |
| 2014/0273067 A1* | 9/2014 | Wanders | G01N 33/5094 435/29 |
| 2014/0273068 A1* | 9/2014 | Wanders | G01N 33/5094 435/29 |
| 2016/0011094 A1* | 1/2016 | Kennington | G01N 15/1404 250/200 |
| 2016/0011096 A1* | 1/2016 | Vacca | G01N 15/1404 356/442 |
| 2017/0109879 A1* | 4/2017 | Urbano | G06T 7/0012 |

FOREIGN PATENT DOCUMENTS

| | | |
|---|---|---|
| JP | S62-124440 A | 6/1987 |
| JP | S63-047633 A | 2/1988 |
| JP | H02-095241 A | 4/1990 |
| JP | H04-188042 A | 7/1992 |
| JP | 8-128944 A | 5/1996 |
| JP | H08-145870 A | 6/1996 |
| JP | 8-219975 A | 8/1996 |
| JP | H09-311102 A | 12/1997 |
| JP | 11-94727 A | 4/1999 |
| JP | 2001-050887 A | 2/2001 |
| JP | 2002-62251 A | 2/2002 |
| JP | 2004-257756 A | 9/2004 |
| JP | 2009-145147 A | 7/2009 |
| JP | 2009-162650 A | 7/2009 |
| JP | 2010-181189 A | 8/2010 |
| JP | 2011-505578 A | 2/2011 |
| JP | 2013-522629 A | 6/2013 |
| WO | 2010-140460 A1 | 12/2010 |

* cited by examiner

FLOW ANALYZER, FLOW CYTOMETER AND FLOW ANALYZING METHOD

CROSS-REFERENCE TO RELATED APPLICATION(S)

The present application claims priority from Japanese Patent Application No. 2014-222144 filed on Oct. 31, 2014, the entire content of which is incorporated herein by reference.

BACKGROUND

The presently disclosed subject matter relates to a flow analyzer, a flow cytometer, and a flow analyzing method.

Flow cytometers are used when analyzing cells or the like. With a flow cytometer, sample liquid containing cells and particles is passed through a flow path called a flow cell, and the cells are analyzed by an image processing. When using a flow cytometer, it is important to accurately detect an abnormality in the flow path system (the location, width, and the like of a sample flow in the flow cell), and to correct the flow path system when there is an abnormality.

For example, JPH08-219975A discloses a particle image analyzer configured to detect an abnormality in an optical system or in a flow path system. The particle image analyzer irradiates an observation target region in a flow cell with light, and acquires a light intensity distribution of an image of particles (particle image) obtained through the irradiation to detect an abnormal state. JPH11-94727A discloses a flow-type particle image analyzer configured to irradiate a flow cell by a flash lamp like the analyzer of JPH08-219975A, and to analyze a particle image obtained by imaging the flow cell to analyze the sample flow. JP2002-062251A discloses a flow-type particle image analyzer configured to also irradiate a sample flow by a flash lamp to take a particle image, and to analyze the particle image to estimate a pattern of the sample flow.

In the related art described above, an abnormality in a flow path system is analyzed by using an imaging system that takes an image of a flow cell irradiated by a flash lamp. However, in a case where there is an abnormality in the imaging system, the flow path system cannot be assessed accurately. For example, it is possible that a distance between a camera and the flow cell or a position (in a depth direction and/or in a lateral direction) of an imaging location slightly changes due to a vibration or an unintended contact with the camera. When there is such an abnormality in the imaging system, a location through which particles pass in the flow cell cannot be detected accurately, and whether the sample flow passes through the center line of the flow cell cannot be evaluated accurately. The imaging system may be adjusted to address such issues (see, e.g., paragraph 0091 of JP2002-62251A), but such fine adjustment takes time and effort.

That is, the related art described above does not address a case where there is an abnormality (deviation) in an imaging system, in terms of accurately evaluating a sample flow.

SUMMARY

Illustrative aspects of the present invention provide a flow analyzer, flow cytometer, and flow analyzing method that can accurately evaluate a sample flow.

According to an illustrative aspect of the present invention, a flow analyzer includes a flash lamp configured to irradiate a flow cell having a flow path with flash light, the flow path having a predetermined width, an imaging section configured to take images of the flow cell that is irradiated by the flash lamp such that the predetermined width is included in an imaging range, an evaluator configured to detect edges indicating respective sides of the flow cell from an image of a fluid that is taken by the imaging section and to evaluate the fluid passing through the flow cell based on a relationship between a width between the detected edges and the predetermined width, and an output section configured to output a result of the evaluation by the evaluator.

The flow analyzer uses the relationship between the width of the flow cell (fixed information) and the edges indicating the respective sides of the flow cell to evaluate, for example, a particle size and/or a location of the fluid in the flow cell. This makes it possible to accurately evaluate, for example, a location and/or size of a particle in the flow cell, even in a case where the imaging position of the imaging section is changed.

DETAILED DESCRIPTION

Figure 1:
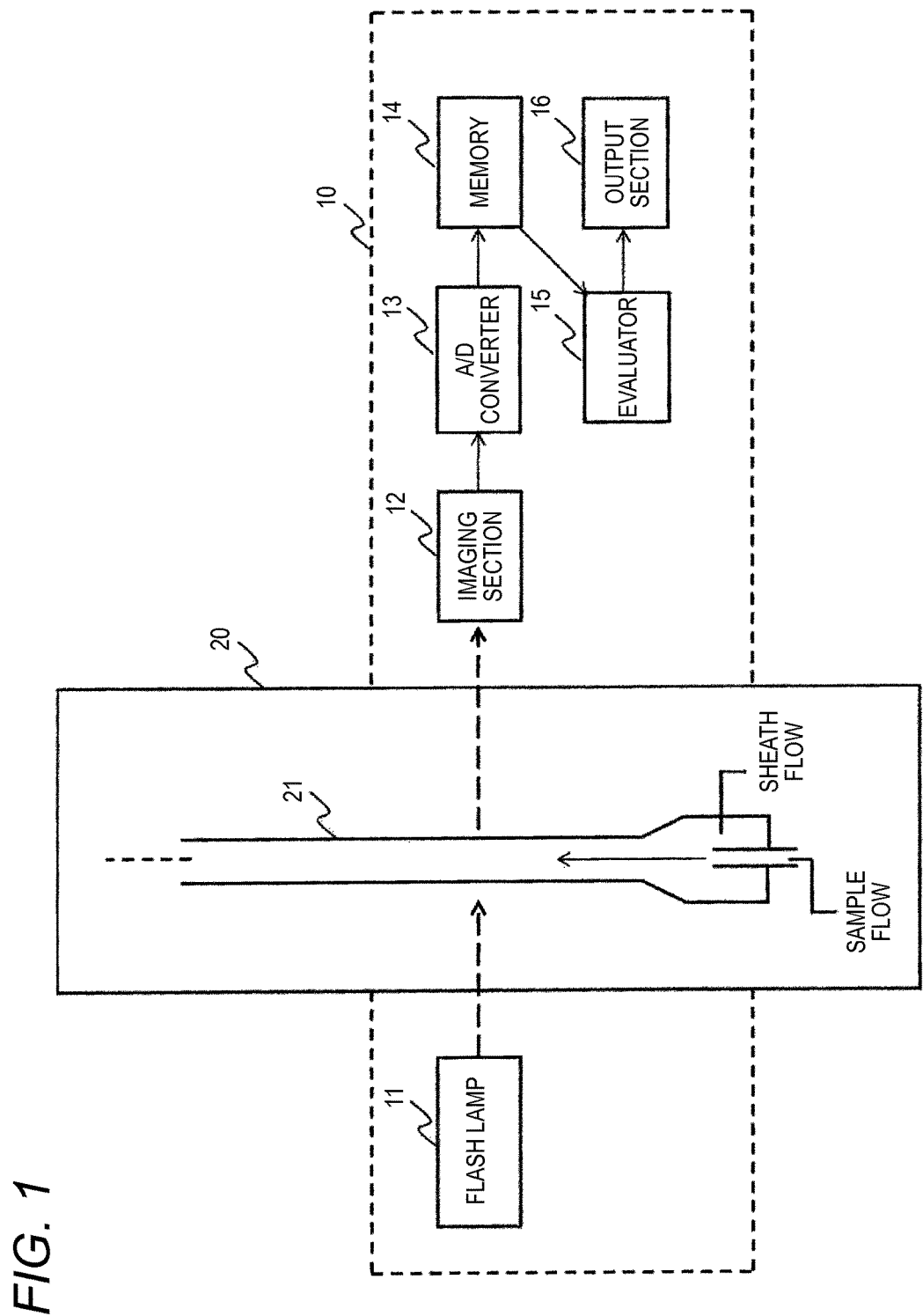
FIG. 1 is a block diagram illustrating configurations of a flow analyzer and a flow cytometer according to an exemplary embodiment according to the present invention.

Hereinafter, exemplary embodiments of the present invention will be described with reference to the drawings. FIG. 1 is a block diagram illustrating configurations of a flow analyzer 10 and a flow cytometer 20 according to an exemplary embodiment of the present invention.

Firstly, the flow cytometer 20 will be described. In the flow cytometer 20, a sample liquid (hereinafter, also described as a sample flow) containing cells and particles (hereinafter, simply described as particles as a term referring to a concept including cells) is passed through a small rectangular hole called a flow cell 21 to evaluate the fluid. The flow cytometer 20 incorporates a laser irradiating apparatus (not shown), and the flow cell 21 through which the sample flow flows is irradiated with laser light. The flow cytometer 20 evaluates scattered light or fluorescence obtained as a result of the laser irradiation, to detect the shape, size, and the like of particles contained in the sample flow. Although description of the internal configuration of the flow cytometer 20 is omitted here, the flow cytometer 20 may, for example, have a configuration disclosed JPH08-128944A.

The laser light which is used in the flow cytometer 20 has a so-called Gaussian shape (the intensity in the center is high, and that in the base is weak). Since the laser light has a Gaussian shape, even when the same particle passes through the flow cell 21, the signal intensity of the particle passing while deviating from the center line of the flow cell 21 is reduced. In other words, the location where the particles pass in the flow cell 21 affects the measurement accuracy. This problem will be described in detail with reference to FIG. 2.

Figure 2:
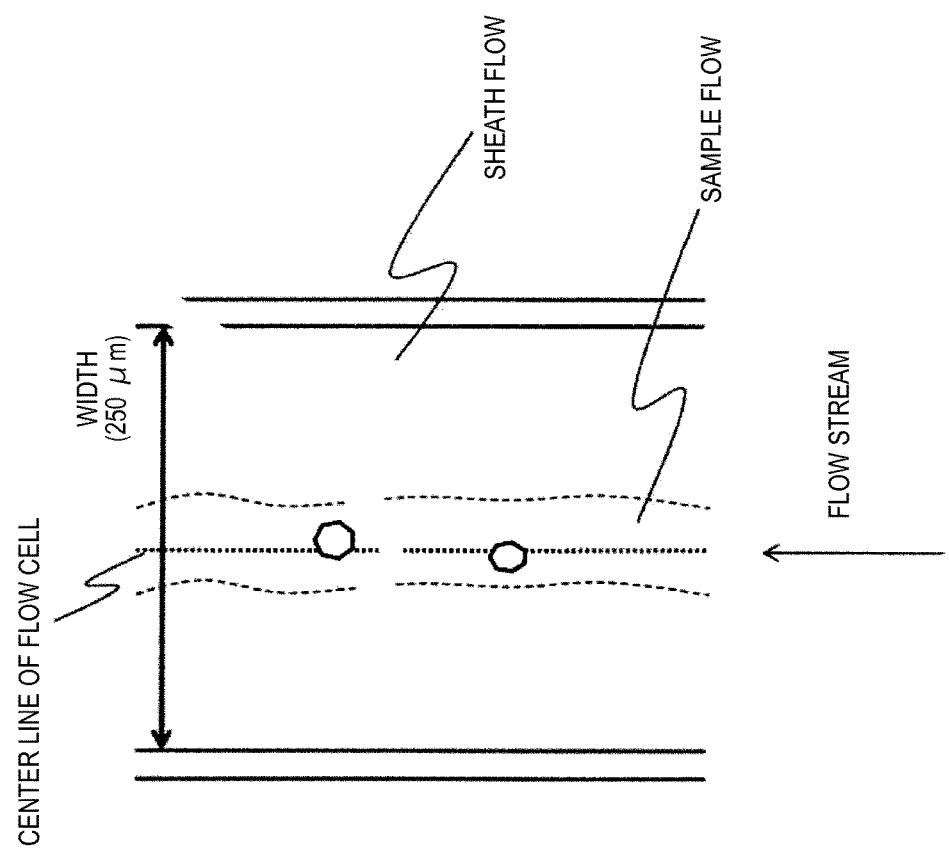
FIG. 2 is a conceptual diagram illustrating a sheath flow and sample liquid passing through a flow cell.

FIG. 2 is a conceptual diagram illustrating a sheath flow and sample flow passing through the flow cell 21. FIG. 2 is merely a conceptual diagram, and sizes and the like are illustrated in a simplified manner. The flow cell 21 is a flow path having a predetermined width. In the illustrated example, the width is 250 µm. In the flow cytometer 20, a sample is stored in a sample vessel which is not shown, the sample is passed through the flow cell 21 as the sample flow after being stained. In addition, a sheath flow is passed through the flow cell 21 such that the sheath flow surrounds the sample flow.

As described above, the laser light which is used in the flow cytometer 20 has a Gaussian shape. Therefore, it is preferred that particles contained in the sample flow pass through the center line of the flow cell 21. Since particles pass through the vicinity of the center line of the flow cell 21, it is desired that the sample flow is located in the vicinity of the center line of the flow cell 21. In the case where the sample flow fails to pass through the vicinity of the center line of the flow cell 21, i.e., the case where particles do not pass through the vicinity of the center line of the flow cell 21, scattered light or fluorescence obtained as a result of the laser irradiation is in an unintended state, with the result that the accuracy of the result of particle classification is degraded. The flow analyzer 10 is used to determine the situation that causes the accuracy degradation in advance. Specifically, the flow analyzer 10 evaluates the fluid (the location of the sample flow, the width of the sample flow, the location where the particles pass, the particle size, and the like) in the flow cell 21.

Referring again to FIG. 1, the flow analyzer 10 has a flash lamp 11, an imaging section 12, an analog/digital (A/D) converter 13, a memory 14, an evaluator 15, and an output section 16. The flow analyzer 10 is attachable to and detachable from, for example, the flow cytometer 20. For example, a serviceman who installs and maintains the flow cytometer 20 attaches the flow analyzer 10 to the flow cytometer 20 before the use of the flow cytometer 20. A configuration in which the flow analyzer 10 is incorporated into the flow cytometer 20 will be described later as another exemplary embodiment.

The flash lamp 11 is a lamp for irradiating the flow cell 21 with flash light (strobe light). The flash lamp 11 irradiates the sample flow and sheath flow in the flow cell 21 with flash light. Preferably, the flash lamp 11 emits light 15 or more times per second, and more preferably 30 or more times per second.

The imaging section 12 takes optical images of particles obtained by the light emission of the flash lamp 11. The imaging section 12 includes a lens and a circuit system used in an imaging process. The imaging section 12 takes an optical image of particles obtained by each light emission of the flash lamp 11. In the case where the flash lamp 11 emits light 30 times per second, for example, the imaging section 12 acquires 30 fluid images (still images). The imaging section 12 performs the imaging processing such that each image contains the entire width (250 µm) of the flow cell 21. The imaging section 12 sends the acquired fluid images to the A/D converter 13.

The A/D converter 13 converts the fluid images of analog data into digital data, and stores the digital data in the memory 14. The fluid images are stored in the memory 14 such that each fluid image is associated with its imaging timing (time elapsed after the start of analysis).

The memory 14 stores various data such as the image data obtained in the A/D conversion process. The memory 14 is a storage device such as a hard disk drive (HDD). The memory 14 may be a device installed the flow analyzer 10, or attachable to and detachable from the flow analyzer 10 such as a universal serial bus (USB) memory.

The evaluator 15 sequentially reads out the fluid images from the memory 14, and analyzes the fluid images, thereby evaluating the fluid in the flow cell 21. Specifically, the evaluator 15 detects the edges of each fluid image, and evaluates the fluid in the flow cell 21 based on the relationships between the width (250 µm) of the flow cell 21 and the detected edges. This evaluation will be described in detail with reference to FIG. 3.

Figure 3:
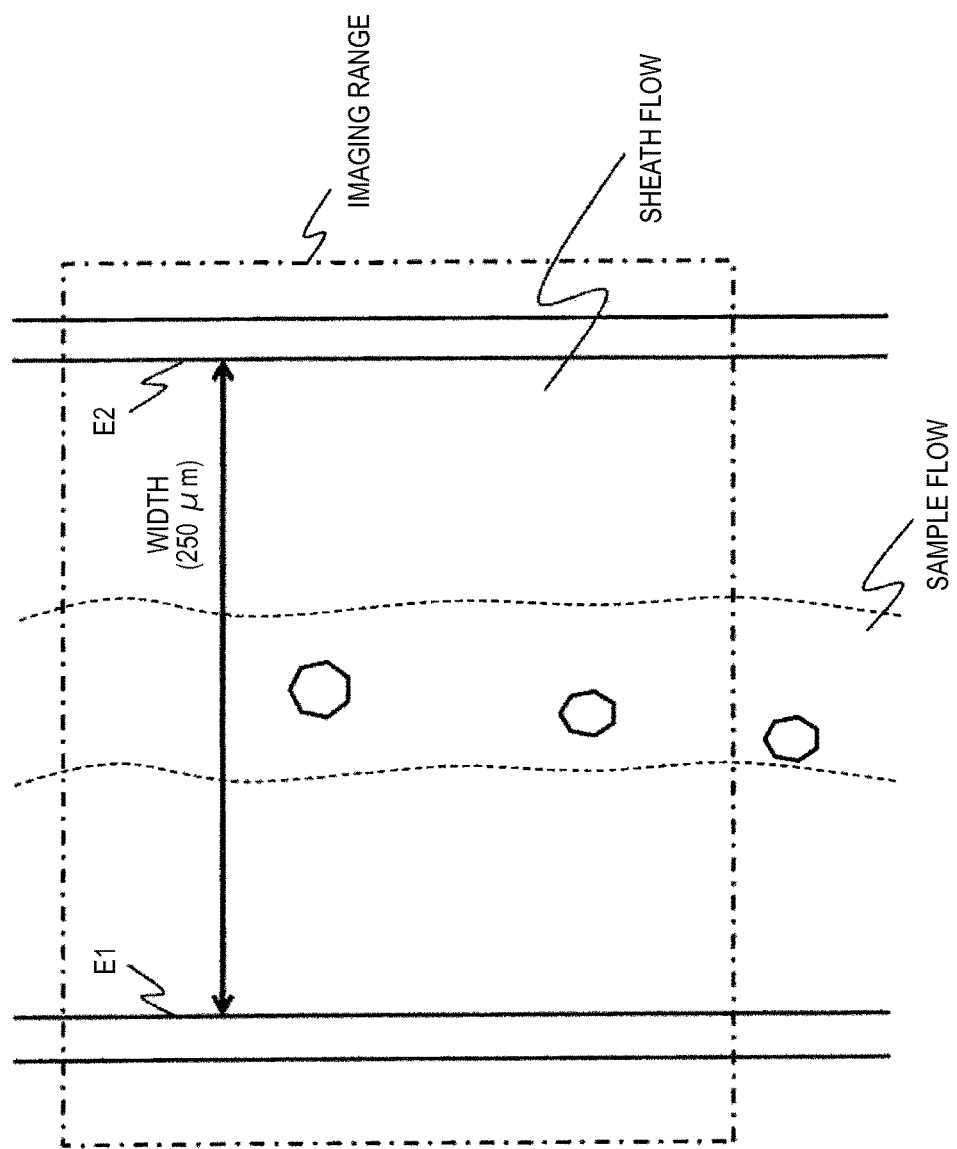
FIG. 3 is a conceptual diagram illustrating how an evaluator evaluates a sample flow.

As a premise, the imaging section 12 performs the imaging process with the imaging range defined so as to include the entire width of the flow cell 21 (e.g., the region indicated by the dash-dot line in FIG. 3 is set as the imaging range), to acquire a fluid image. From the fluid image, the evaluator 15 detects the edges (E1 and E2 in FIG. 3) at the both sides of the flow cell 21. That is, the evaluator 15 detects the respective sides of the flow cell 21 from changes in luminance in the fluid image, and based on the detected sides, detects a portion corresponding to the width of the flow cell 21. To detect the edges, a method used in a field of typical image analysis may be used (e.g., a detection method using the change rate of the luminance or the like).

The evaluator 15 calculates the number of pixels of the portion corresponding to the width of the flow cell 21. In the present example, the width of the flow cell 21 has 1,000 pixels. The evaluator 15 reads out information of the width of the flow cell 21 (e.g., the diameter of 250 µm) previously stored in the memory 14. The evaluator 15 determines a dimension that corresponds to 1 pixel based on the width information (250 µm) of the flow cell 21. In this example, the evaluator 15 calculates that 1 pixel corresponds to 0.25 µm (formulates a conversion equation of "1 pixel=0.25 µm").

Figure 4A:
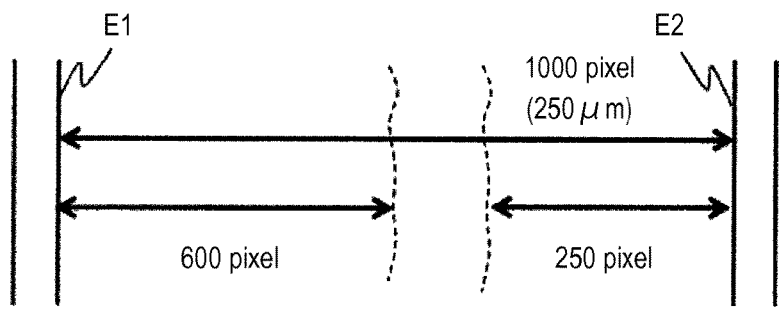
FIGS. 4A and 4B are other conceptual diagrams illustrating how the evaluator evaluates the sample flow.
Figure 4B:
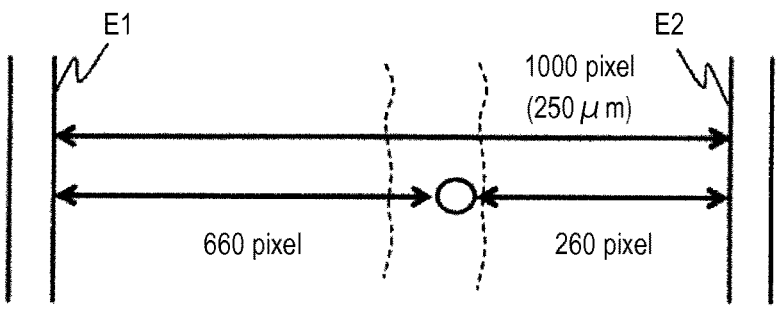

The evaluator 15 evaluates the fluid based on this pixel conversion system (1 pixel=0.25 µm). Firstly, a method of evaluating the width and location of the sample flow will be described with reference to FIG. 4A. In FIGS. 4A and 4B, in order to clarify the illustration, the sample flow and the particle size are illustrated to be larger than the actual relative size.

In the example of FIG. 4A, the evaluator 15 first calculates that 1 pixel corresponds to 0.25 µm (or 4 pixels correspond to 1 µm) as described above. Then, the evaluator 15 detects the edges of the sample flow. The evaluator 15 detects that one edge of the sample flow is at a location away from one edge of the flow cell 21 by 600 pixels, and that the other edge of the sample flow is at a location away from the other edge of the flow cell 21 by 250 pixels. Based on this detection, the evaluator 15 calculates that the width of the sample flow is 150 pixels, i.e., 37.5 µm. Moreover, evaluator 15 calculates that the center of the sample flow is at a location away from the one edge of the flow cell 21 by 675 pixels (600+(150/2), i.e., the location shifted from the center of the flow cell 21 by 175 pixels (the location deviated from the center by 43.75 µm).

In a similar manner as the sample flow, the evaluator 15 calculates the location where the particles pass, the particle size, and the like. A method of calculating the location where the particles pass and the particle size will be described with reference to FIG. 4B. In the example of FIG. 4B, the evaluator 15 calculates that 1 pixel corresponds to 0.25 µm (i.e., 4 pixels correspond to 1 µm). The evaluator 15 determines the outline of a passing particle by means of the edge detection. The evaluator 15 detects that one side of the passing particle is at a location away from the one edge of the flow cell 21 by 660 pixels, and that the other side of the passing particle is at a location away from the other edge of the flow cell 21 by 260 pixels. Based on this detection, the evaluator 15 calculates that the size of the passing particle is 80 pixels (1,000 pixels−660 pixels−260 pixels), i.e., 20 µm. Moreover, the evaluator 15 calculates that the location of the passing particle is away from the one edge of the flow cell 21 by 700 (660+(80/2), i.e., the location away from the center of the flow cell 21 by 200 pixels (the location deviated from the center by 50 µm).

The evaluator 15 performs this evaluating processing with respect to each fluid image to calculate a location and width of the sample flow, a locations of a passing particle, size of the passing particle, and the like in each time period. The result of the evaluation by the evaluator 15 is sent to the output section 16.

Referring again to FIG. 1, the output section 16 outputs the result of the evaluation of the fluid in the flow cell 21 by the evaluator 15. Here, "output" has a concept including displaying of the result on a display device (not shown) disposed in the flow analyzer 10, printing of the evaluation result on a printing sheet, transmission of the evaluation result to another apparatus having a display device, and the like.

Figure 5:
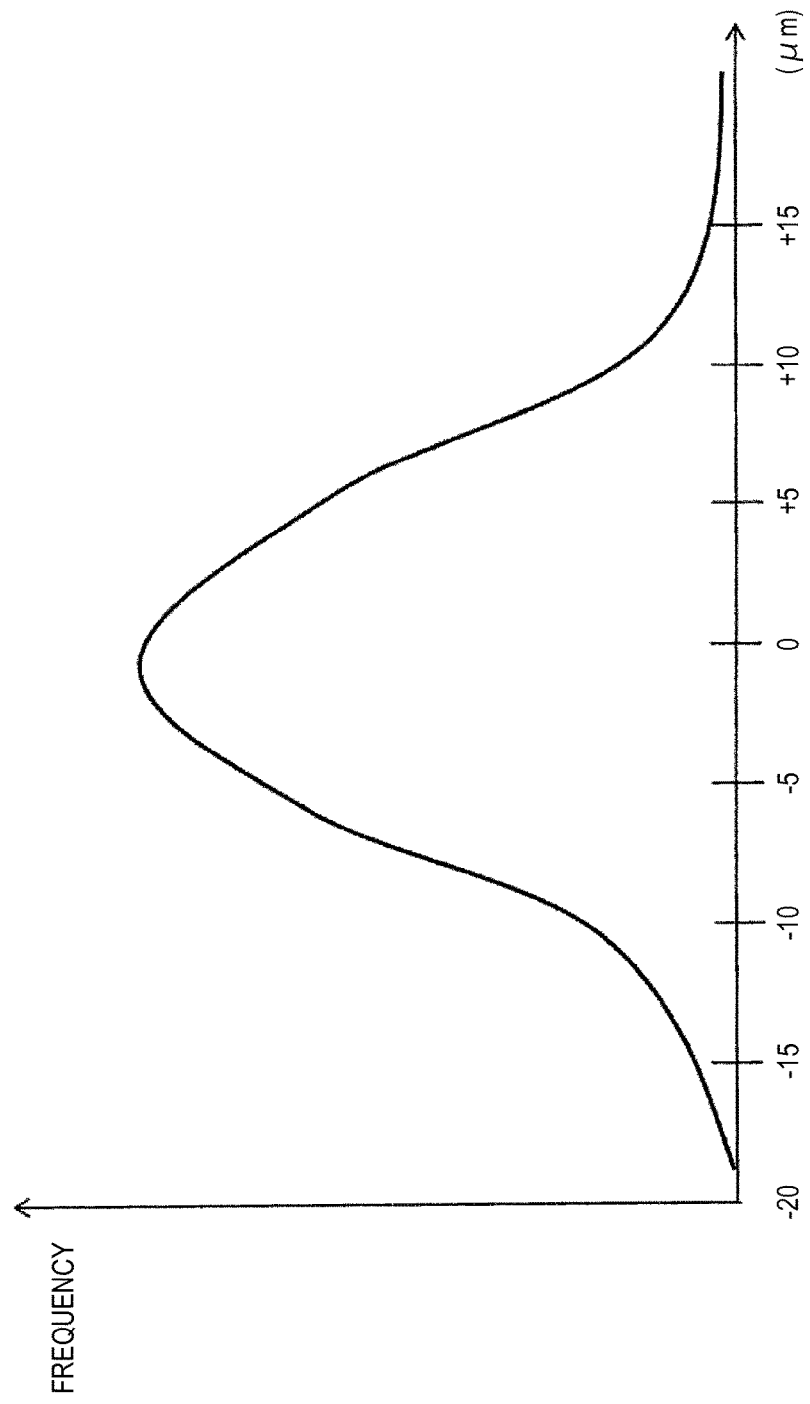
FIG. 5 is a conceptual diagram illustrating an example of an output by an output section.

Hereinafter, an example of the output of the output section 16 will be described with reference to FIGS. 5 to 8. Firstly, an example in which the passing locations of particles are displayed in the form of a histogram will be described with reference to FIG. 5. The evaluator 15 evaluates the fluid images by the above-described method (FIG. 4B), and calculates the passing locations of particles. Then, the output section 16 produces and displays a histogram in which the abscissa represents the location in the flow cell 21 (the center of the flow cell 21 is set to 0 µm, the leftward direction is the minus direction, and the rightward direction is the plus direction), and the ordinate represents the number (frequency) of passing particles (FIG. 5). By referring to the histogram, the user can easily confirm whether particles pass through the center line. In the example of FIG. 5, the frequency in the vicinity of the center position of the flow cell 21 is high, and therefore the user can confirm that the sample flow is in a substantially no problematic state. The output section 16 may not display the histogram on a screen, and may output it in another form such as printing.

Alternatively, the output section 16 may produce a histogram showing locations where particles pass in unit time. Hereinafter, such a histogram will be described in detail.

Figure 6:
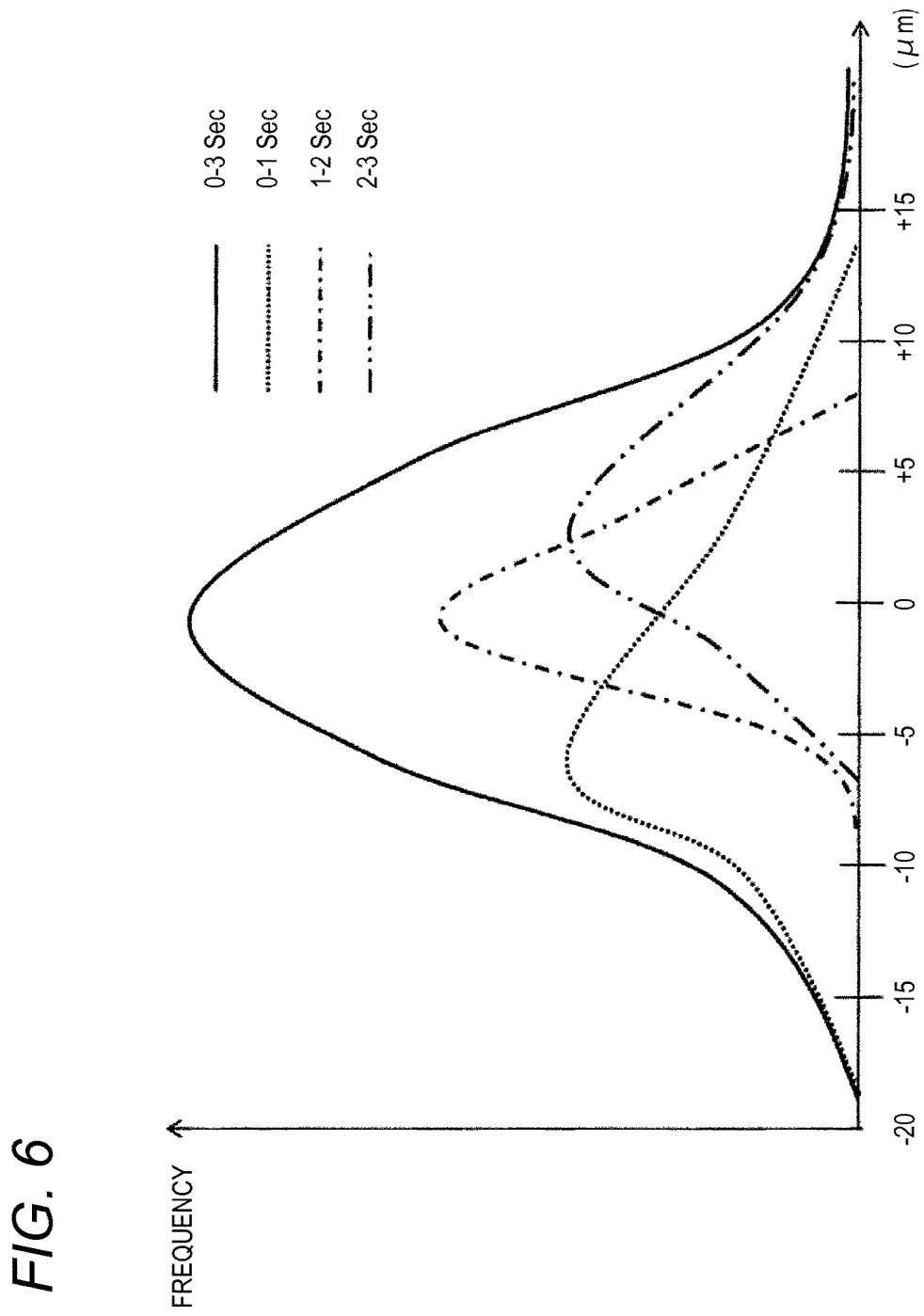
FIG. 6 is a conceptual diagram illustrating another example of an output by the output section.

FIG. 6 is an example of a histogram showing locations where particles pass in each unit time. The imaging section 12 takes a fluid image in each light emission of the flash lamp 11. Each fluid image is associated with the imaging timing (time elapsed after start of analysis of the sample flow). In the example shown in FIG. 6, the analysis is performed for three seconds, and locations where particles pass in each unit time (0 to 1 second, 1 to 2 seconds, and 2 to 3 seconds after start of analysis of the sample flow) are displayed.

The evaluator 15 evaluates the fluid images of the units of time (0 to 1 second, 1 to 2 seconds, and 2 to 3 seconds), and counts the number of passing particles. The output section 16 outputs a result of the counting of passing particles as a histogram in each unit time (FIG. 6). The output section 16 may output also a histogram showing the number of passing particle in the time period (0 to 3 seconds) from the start of the analysis to the end of the analysis (FIG. 6).

By referring to the solid-line histogram in FIG. 6, the user can see that, in the entire time period, many particles pass through the center line and its vicinity of the flow cell 21. However, by referring to the histograms (of the broken line, the dash-dot line, and the dash-dot-dash line) of the respective unit time, the user can see that the locations where the particles pass are gradually shifted from a minus area to a plus area. Therefore, the user can confirm that the cytometry is performed with the flow cytometer 20 being in an improper condition (e.g., the flow cytometer 20 being slightly inclined).

Figure 7:
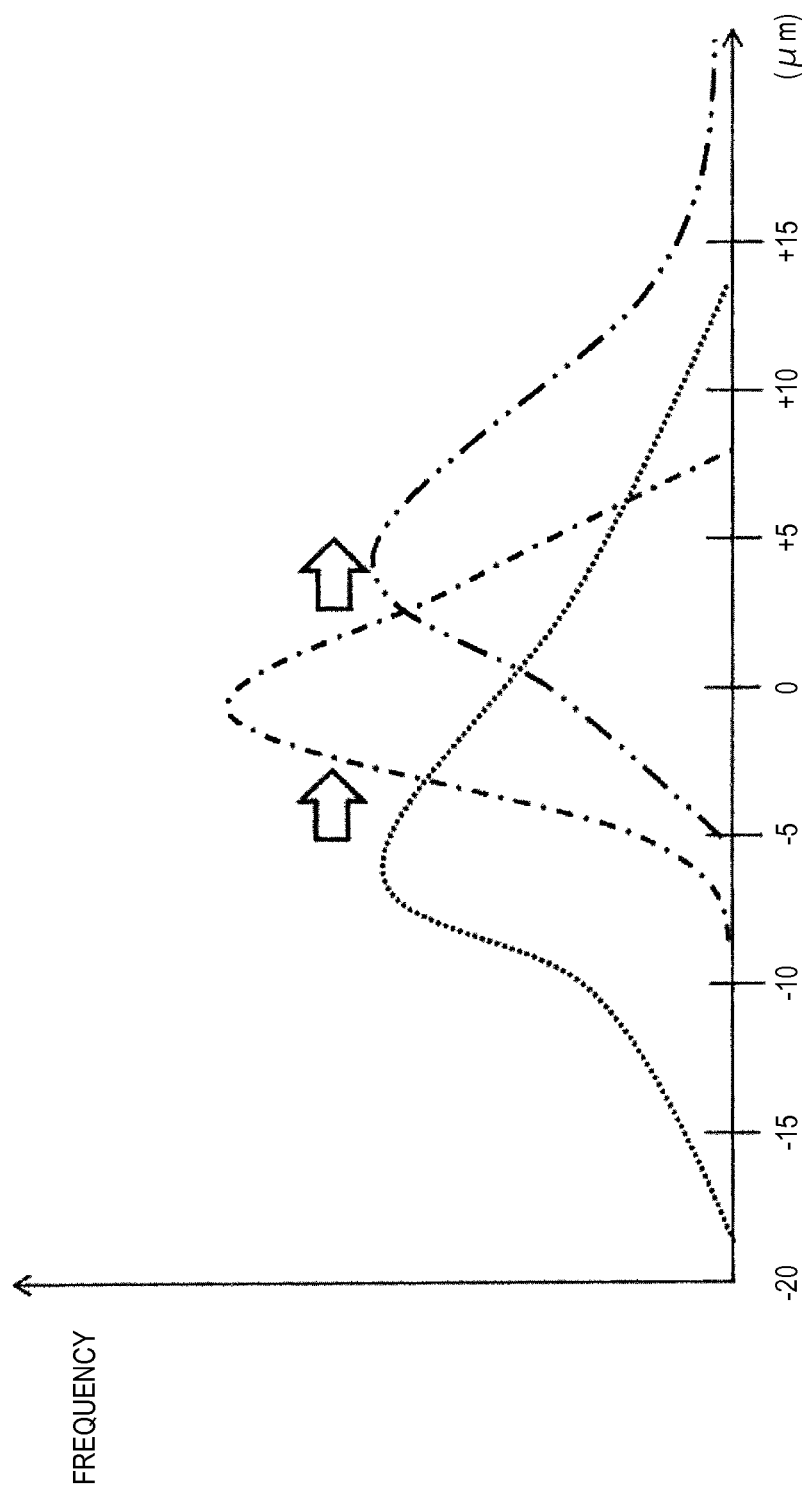
FIG. 7 is a conceptual diagram illustrating another example of an output by the output section.

Instead of displaying the histograms of each unit time by using still images as shown in FIG. 6, an animation (moving image) in which a histogram is moved as shown in FIG. 7 may be displayed.

Figure 8:
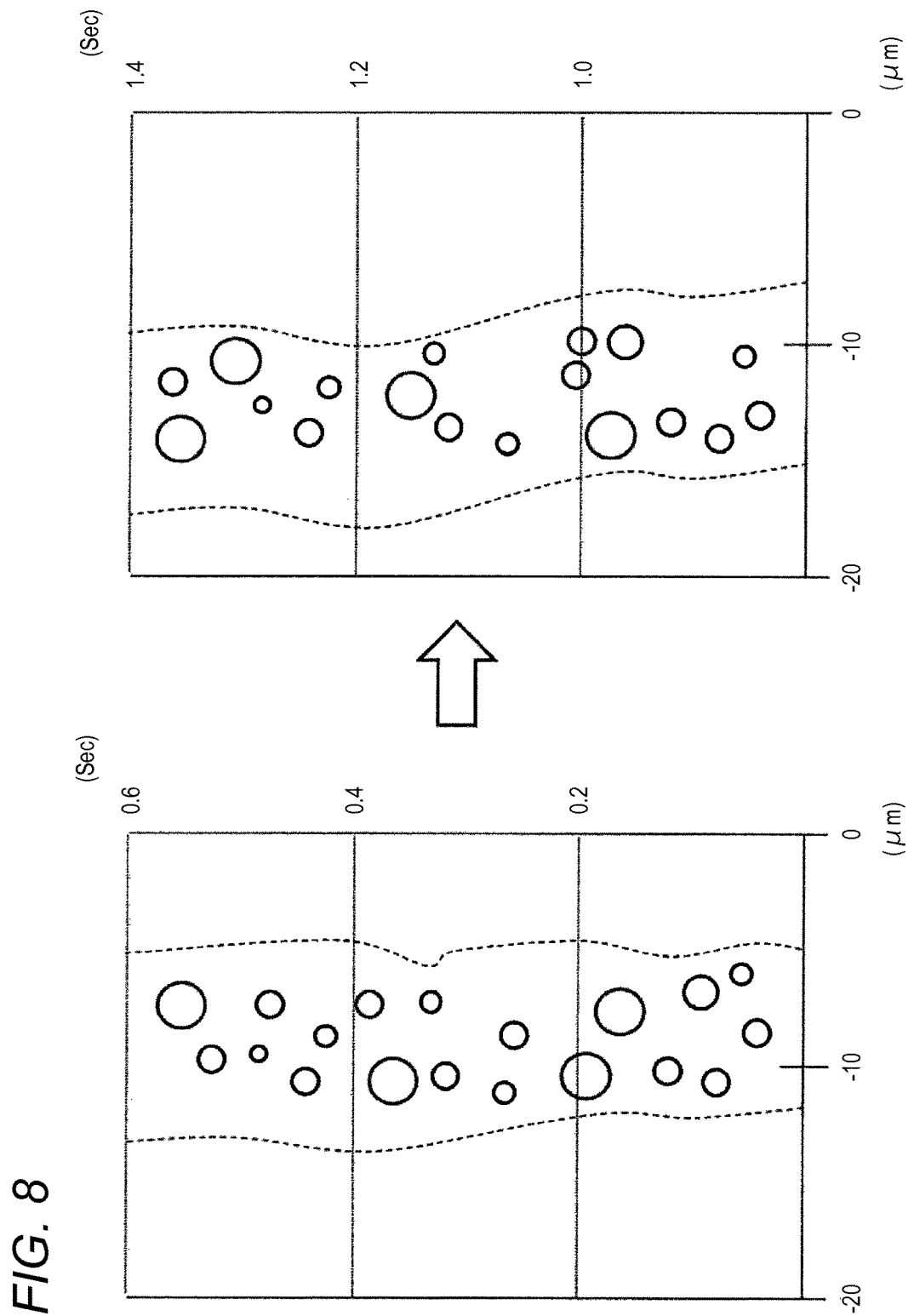
FIG. 8 is a conceptual diagram illustrating another example of the output by the output section.

Referring to FIG. 8, a second example of the output of the output section 16 will be described. In the second output example, the position and width of the sample flow, and the passing locations and sizes of particles are displayed in the form of animation (moving image). In FIG. 8, the center position of the flow cell 21 is set to 0 µm, the leftward direction is the minus direction, and the rightward direction is the plus direction.

By using the above-described technique, the evaluator 15 calculates the position and width of the sample flow, and the passing locations and sizes of particles in each elapsed time. The output section 16 displays the transition of the sample flow and particles, in the form of animation by using the calculated information. FIG. 8 shows a display example of the animation, and is a conceptual diagram illustrating the animation in which the sample flow and particles flow from the upper side of the figure to the lower side.

By referring to the animation, the user can intuitively see the sample flow and the flow of particles. In the example of FIG. 8, for example, the user can see that the location of the sample flow is gradually shifting in the minus direction, in the form of animation.

The output form is not limited to an animation. The output section 16 may output transitions of the sample flow and particles between timings (e.g., 0 to 0.6 seconds) designated by the user, in the form of a still image (i.e., the left image in FIG. 8). Although, in the example of FIG. 8, both the sample flow and passing particles are displayed, the display manner is not limited to this, and only one of the sample flow and passing particles may be displayed in accordance with mode switching.

Then, effects of the flow analyzer 10 of the exemplary embodiment will be described. The evaluator 15 of the flow analyzer 10 sets a constant value or the width (in the above-described example, 250 µm) of the flow cell 21, as the reference. The width of the flow cell 21 is an absolute value which is not changed even when an abnormality (e.g., a positional deviation of the camera, or contact with the camera) occurs in the imaging section 12. The evaluator 15 evaluates the fluid in the flow cell (e.g., the width and location of the sample flow, locations where particles pass, and sizes of the particles) based on a relationship of the width of the flow cell 21 with the edges affected by the sample flow and particles. That is, the evaluator 15 evaluates the sample flow by using the fixed information regarding the width of the flow cell 21 even in a case where an abnormality occurs in the imaging system. Therefore, it is possible to realize an accurate evaluation of the fluid in the flow cell 21 even in a case where an abnormality (deviation) occurs in the imaging system.

The output section 16 outputs a result of the fluid evaluation by the evaluator 15 in various formats. For example, the output section 16 displays positions through which particles pass in the flow cell 21, in the form of a histogram as shown in FIG. 5. By referring to the histogram (FIG. 5), the user can easily confirm a relationship between locations and numbers of particles passing in the flow cell 21.

The output section 16 divides the analyzed time into units of time (e.g., 0 to 1 second, 1 to 2 seconds, and 2 to 3 seconds as shown in FIG. 6), produces a plurality of histograms indicating passing locations and numbers of particles in the flow cell 21 in the respective units of time, and displays the plurality of histograms in a superimposed manner (FIG. 6). By referring to the histograms (FIG. 6), the user can intuitively confirm a relationship between the time lapse and passing locations of particles. Also by displaying the plurality of produced histograms in the form of animation (FIG. 7), it is possible to intuitively confirm the relationship between the time lapse and the passing locations of the particles.

The output section 16 may display temporal changes of the detected locations of the edges indicating the respective sides of the sample flow passing through the flow cell 21 (FIG. 8). In the example of FIG. 8, the output section 16 displays temporal changes of the edges of the sample flow while the ordinate represents the elapsed time, and the abscissa represents the position in the flow cell 21. Similarly, the output section 16 displays temporal changes of the passing locations of particles while the ordinate represents the elapsed time, and the abscissa represents the position in the flow cell 21. By referring to the display of temporal changes, the user can easily confirm how the sample flow and passing locations of particles change over time.

As described above, the flash lamp 11 emits light at least 15 times per second, and preferably 30 or more times per second. According to the configuration, when an animation or the like is displayed, it is possible to realize a natural display.

A flow cytometer 20 according to another exemplary embodiment of the present invention has the function of the flow analyzer 10 incorporated therein.

Figure 9:
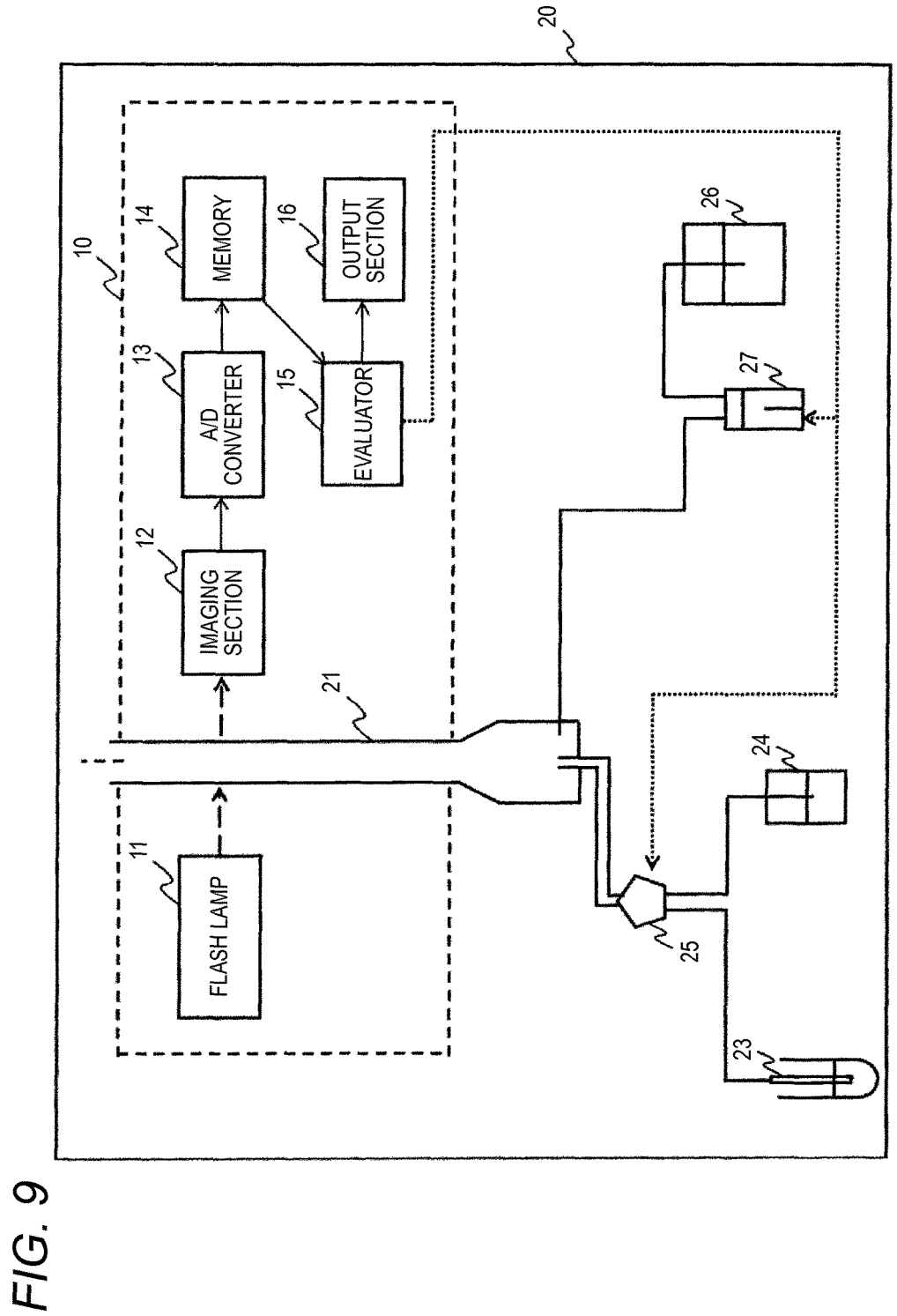
FIG. 9 is a block diagram illustrating a configuration of a flow cytometer according to another exemplary embodiment of the present invention.

FIG. 9 is a block diagram illustrating a configuration of such a flow cytometer 20. In the following description, processing sections denoted by the same reference signs as those of the foregoing exemplary embodiment perform processings similar to those of the foregoing exemplary embodiment unless otherwise specified.

In FIG. 9, processing sections which are in the flow path system of the flow cytometer 20, and which are not illustrated in FIG. 1 are shown. Namely, the flow cytometer 20 has a sample container 22, a sampling nozzle 23, a staining solution 24, a staining tank 25, a sheath fluid container 26, and a sheath fluid delivery syringe 27.

The sample container 22 stores a sample which is to be analyzed. The sampling nozzle 23 is used for sucking the sample from the sample container 22, and storing it in the staining tank 25. Also, the staining solution 24 is supplied to the staining tank 25. In the staining tank 25, particles in the sample are stained.

The sheath fluid container 26 stores a sheath fluid that flows while enveloping the sample. The sheath fluid delivery syringe 27 suctions the sheath fluid from the sheath fluid container 26, and delivers the sucked sheath fluid into the flow cell 21. In place of the sheath fluid delivery syringe 27, a constant fluid delivery type member may be used to suction the sheath fluid and to deliver it to the flow cell 21. The sample stained in the staining tank 25 (i.e., the sample flow) flows through the flow cell 21 so as to be enveloped by the sheath fluid. Although, in the above description, the flow cytometer 20 has the staining solution 24 and the staining tank 25, the configuration is not limited to this, and a configuration where the flow analyzer 10 is incorporated in the flow cytometer 20 that is not provided with the staining solution 24 and the staining tank 25 may be employed.

The above-described flow system in the exemplary embodiment adjusts the flow rate of the sample flow, and the inflow position in accordance with a result of the evaluation by the evaluator 15.

During the analysis by the flow cytometer 20, the processing sections of the flow analyzer 10 perform the sample flow analysis described above (evaluations of the location of the sample flow, the width of the sample flow, locations where particles pass, and sizes of the passing particles). The evaluator 15 in the exemplary embodiment performs a feedback control in accordance with results of the evaluations. When the width of the sample flow is equal to or larger than a predetermined value, for example, the evaluator 15 sends control instructions for reducing the flow rate, to the flow out system of the staining tank 25. In the case where the location where the sample flow passes is deviated from the center line of the flow cell 21, the evaluator 15 sends instructions to the flow out system of the staining tank 25 to adjust the flow out position.

Similarly, the evaluator 15 may issue instructions for adjusting the flow out system of the staining tank 25 in accordance with the positions and number of passing particles. Moreover, the evaluator 15 may issue instructions for adjusting the sheath fluid delivery system (the sheath fluid delivery syringe 27 and the like) in accordance with a result of the analysis of the sample flow.

The operation of the flow cytometer 20 of the exemplary embodiment has been described above. Now, the effect of the flow cytometer 20 of the exemplary embodiment will be described. In the exemplary embodiment, during the particle analysis (analysis using scattered light or fluorescence) by the flow cytometer 20, the flow analyzer 10 performs the sample flow analysis (evaluation of the position of the sample flow, that of the width of the sample flow, that of passing locations of particles, and that of sizes of passing particles), and the flow rate and inflow position of the sample flow are adjusted in accordance with a result of the sample flow analysis. In other words, the flow cytometer 20 of the exemplary embodiment has a function of automatically correcting the sample flow. Therefore, the flow cytometer 20 can perform highly accurate particle analysis.

While the present invention has been described with reference to certain exemplary embodiments thereof, the scope of the present invention is not limited to the exemplary embodiments described above, and it will be understood by those skilled in the art that various changes and modifications may be made therein without departing from the scope of the present invention as defined by the appended claims.

What is claimed is:

1. A flow analyzer comprising:
a flash lamp configured to irradiate a flow cell with flash light, the flow cell having a flow path of a predetermined width;
an imaging section configured to take images of the flow cell that is irradiated by the flash lamp such that the predetermined width is included in an imaging range;
an evaluator configured to detect edges indicating respective sides of the flow cell from an image of a fluid that is taken by the imaging section, to calculate a number of pixels between the detected edges at the respective sides of the flow cell, to formulate a conversion equation from a pixel to an actual dimension based on the calculated number of pixels and the predetermined width, and to evaluate the fluid passing through the flow cell, based on the conversion equation; and
an output section configured to output a result of the evaluation by the evaluator.

2. The flow analyzer according to claim 1,
wherein the evaluator is configured to calculate, using the conversion equation, at least one of a width of a sample flow passing through the flow cell, a location where the sample flow passes, locations of particles passing through the flow cell, and sizes of the particles passing through the flow cell, to provide the result of the evaluation.

3. The flow analyzer according to claim 2, wherein the detector is configured to detect edges of the sample flow to calculate at least one of the width of the sample flow passing through the flow cell and the location where the sample flow passes.

4. The flow analyzer according to claim 2, wherein the detector is configured to determine an edge indicating an outline of each particle to calculate the locations of particles passing through the flow cell, and the sizes of the particles passing through the flow cell.

5. The flow analyzer according to claim 1, wherein the evaluator is configured to detect locations of particles passing through the flow cell, based on a detection of an edge indicating an outline of a particle, and
wherein the output section is configured to produce a histogram indicating a relationship between the locations of the particles passing through the flow cell and numbers of the particles passing through the respective locations, based on the locations of the particles detected by the evaluator, and to output the produced histogram.

6. The flow analyzer according to claim 5, wherein the output section is configured to produce the histogram indicating the relationship between the locations of the particles passing through the flow cell and the numbers of the particles passing through the respective locations in each unit time, and to display a plurality of produced histograms in a superimposed manner.

7. The flow analyzer according to claim 5, wherein the output section is configured to produce the histogram indicating the relationship between the locations of the particles through the flow cell and the numbers and of the particles passing through the respective locations in each unit time, and to display a plurality of produced histograms in a form of animation.

8. The flow analyzer according to claim 1, wherein the evaluator is configured to detect a location of an edge of the sample flow in the flow cell, and
wherein the output section is configured to display a temporal change of the location of the edge of the sample flow detected by the evaluator.

9. The flow analyzer according to claim 1, wherein the evaluator is configured to detect locations of particles passing through the flow cell, based on a detection of an edge indicating an outline of a particle, and
wherein the output section is configured to display temporal changes of the locations of the particles passing through the flow cell and detected by the evaluator.

10. The flow analyzer according to claim 1, wherein the flash lamp is configured to emit the flash light at least 15 times per second.

11. The flow analyzer according to claim 1, wherein the output section is configured to display the result on a display device, to print the result on a sheet, or to transmit the result to a different apparatus.

12. A flow cytometer comprising:
a flow cell comprising a flow path through which a sample flow containing a sample liquid and a sheath flow are passed, and the flow path having a predetermined width;
a flash lamp configured to irradiate the flow cell with flash light;
an imaging section configured to take images of the flow cell that is irradiated by the flash lamp such that the predetermined width is included in an imaging range;
an evaluator configured to detect edges indicating respective sides of the flow cell from an image of a fluid that is taken by the imaging section, to calculate a number of pixels between the detected edges at the respective sides of the flow cell, to formulate a conversion equation from a pixel to an actual dimension based on the calculated number of pixels and the predetermined width, and to evaluate the fluid passing through the flow cell, based on the conversion equation; and
an output section configured to output a result of the evaluation by the evaluator.

13. The flow cytometer according to claim 12, wherein an inflow of the sample flow or the sheath flow is adjusted based on the evaluation of the fluid by the evaluator.

14. A flow analyzing method comprising:
irradiating a flow cell having a flow path of a predetermined width with flash light;
taking images of the irradiated flow cell such that the predetermined width is included in an imaging range;
detecting edges indicating respective sides of the flow cell from an image of a fluid that is obtained in the step of taking the images;
calculating a number of pixels between the detected edges at the respective edges of the flow cell;
formulating a conversion equation from a pixel to an actual dimension based on the calculated number of pixels and the predetermined width;
evaluating the fluid through the flow cell based on the conversion equation; and
outputting a result of the evaluation.

* * * * *